US00PP29002P2

(12) United States Plant Patent
Misato

(10) Patent No.: US PP29,002 P2
(45) Date of Patent: Feb. 27, 2018

(54) ***MANDEVILLA* PLANT NAMED 'SUNPA 1463'**

(50) Latin Name: *Mandevilla hybrida*
Varietal Denomination: Sunpa 1463

(71) Applicant: Tomoya Misato, Shiga (JP)

(72) Inventor: Tomoya Misato, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 15/530,378

(22) Filed: Jan. 4, 2017

(51) Int. Cl.
*A01H 5/02* (2006.01)

(52) U.S. Cl.
USPC ..... Plt./232

(58) Field of Classification Search
USPC ..... Plt./232
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Mandevilla* plant named 'Sunpa 1463', characterized by its semi-climbing plant habit; vigorous growth habit; freely branching habit; relatively large leaves; early and freely flowering habit; long flowering period; and large red-colored flowers.

1 Drawing Sheet

Botanical designation: *Mandevilla hybrida.*
Cultivar denomination: 'SUNPA 1463'.

BACKGROUND OF THE INVENTION

The present invention relates to a new and distinct cultivar of *Mandevilla* plant, botanically known as *Mandevilla hybrida* and hereinafter referred to by the name 'Sunpa 1463'.

The new *Mandevilla* plant is a product of a planned breeding program conducted by the Inventor in Higashiomi, Shiga, Japan. The objective of the breeding program is to create new semi-climbing and freely branching *Mandevilla* plants with freely flowering habit and large attractive flowers.

The new *Mandevilla* plant originated from a cross-pollination in Higashiomi, Shiga, Japan in May, 2009 of a proprietary selection of *Mandevilla hybrida* identified as code number 04M11-2, not patented, as the female, or seed parent with a proprietary selection of *Mandevilla hybrida* identified as code number M37-1, not patented, as the male, or pollen, parent. The new *Mandevilla* plant was discovered and selected by the Inventor as a single flowering plant from within the progeny of the stated cross-pollination in a controlled greenhouse environment in Higashiomi, Shiga, Japan in September, 2010.

Asexual reproduction of the new *Mandevilla* plant by terminal vegetative cuttings in Higashiomi, Shiga, Japan since March, 2011 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunpa 1463'. These characteristics in combination distinguish 'Sunpa 1463' as a new and distinct *Mandevilla* plant:

1. Semi-climbing plant habit.
2. Vigorous growth habit.
3. Freely branching habit.
4. Relatively large leaves.
5. Early and freely flowering habit.
6. Long flowering period.
7. Large red-colored flowers.

Plants of the new *Mandevilla* can be compared to plants of the female parent selection. Plants of the new *Mandevilla* differ primarily from plants of the female parent selection in the following characteristics:

1. Plants of the new *Mandevilla* have larger flowers than plants of the female parent selection.
2. Plants of the new *Mandevilla* and the female parent selection differ in flower color as plants of the female parent selection have white-colored flowers.

Plants of the new *Mandevilla* can be compared to plants of the male parent selection. Plants of the new *Mandevilla* differ primarily from plants of the male parent selection in flower size as plants of the new *Mandevilla* have larger flowers than plants of the male parent selection.

Plants of the new *Mandevilla* can be compared to plants of the *Mandevilla hybrida* 'Sunparaoros', disclosed in U.S. Plant Pat. No. 25,207. In side-by-side comparisons, plants of the new *Mandevilla* differ from plants of 'Sunparaoros' in the following characteristics:

1. Plants of the new *Mandevilla* have longer stems than plants of 'Sunparaoros'.
2. Plants of the new *Mandevilla* have larger and more pubescent leaves than plants of 'Sunparaoros'.
3. Flower petals of plants of the new *Mandevilla* are obovate and not imbricate whereas flower petals of plants of 'Sunparaoros' are orbicular and imbricate.

4. Plants of the new *Mandevilla* and 'Sunparaoros' differ in flower color as plants of 'Sunparaoros' have lighter red-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunpa 1463' grown in a container.

The photograph at the bottom of the sheet is a close-up view of a typical flowering plant of 'Sunpa 1463'.

DETAILED BOTANICAL DESCRIPTION

The aforementioned photographs and following observations, measurements and values describe plants grown during the summer in 15-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were six months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunpa 1463'.

Parentage:

*Female, or seed, parent*.—Proprietary selection of *Mandevilla hybrida* identified as code number 04M11-2, not patented.

*Male, or pollen, parent*.—Proprietary selection of *Mandevilla hybrida* identified as code number M37-1, not patented.

Propagation:

*Type*.—By terminal vegetative cuttings.

*Time to initiate roots*.—About two weeks at temperatures about 23° C. to 25° C.

*Time to produce a rooted young plant*.—About five to six weeks at temperatures about 23° C. to 25° C.

*Root description*.—Fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Semi-climbing plant habit; vigorous growth habit; freely branching habit.

*Plant height* (*with support*).—About 182 cm.

*Lateral branch description*.—Length: About 32 cm. Diameter: About 3 mm. Internode length: About 7.5 cm. Strength: Strong, flexible. Texture: Pubescent, rough. Color, developing: Close to 145A; slightly tinged with close to 179B. Color, fully developed: Close to 199A.

Leaf description:

*Arrangement*.—Opposite, simple.

*Length*.—About 7.8 cm.

*Width*.—About 4.4 cm.

*Shape*.—Broadly elliptic.

*Apex*.—Acuminate.

*Base*.—Cordate.

*Margin*.—Entire.

*Texture and luster, upper surface*.—Pubescent, leathery, rough; glossy.

*Texture and luster, lower surface*.—Densely pubescent, leathery, rough; matte.

*Venation pattern*.—Pinnate, reticulate.

*Color*.—Developing leaves, upper surface: Close to 144A. Developing leaves, lower surface: Close to 147B. Fully expanded leaves, upper surface: Close to N137D; venation, close to 145B. Fully expanded leaves, lower surface: Close to 138B; venation, close to 145C.

*Petioles*.—Length: About 8.6 cm. Diameter: About 1.7 mm. Texture, upper and lower surfaces: Pubescent. Color, upper and lower surfaces: Close to 144B.

Flower description:

*Flower type and habit*.—Single salverform flowers arranged in axillary racemes; flowers face mostly upright to outwardly; freely flowering habit with about four to seven flowers per inflorescence and about 108 flowers developing per plant.

*Natural flowering season*.—Early flowering habit, plants begin flowering about six weeks after planting; long flowering period, plants flower continuously from early summer until late autumn in Japan.

*Flower longevity on the plant*.—About seven to ten days; flowers not persistent.

*Fragrance*.—None detected.

*Flower buds*.—Height: About 8.9 cm. Diameter: About 1.5 cm. Shape: Rhombic. Color: Distally, close to 53A; mid-section, close to 53B with stripes, close to 11D; proximally, close to 1D and 150C.

*Flowers*.—Appearance: Salverform; flared trumpet, corolla fused and five-parted; flowers roughly star-shaped. Diameter: About 9.8 cm. Depth (length): About 7.8 cm. Throat diameter: About 2.1 cm. Tube length: About 3.9 cm. Tube diameter, proximally: About 3.8 mm.

*Corolla*.—Quantity and arrangement: Five petals arranged in a single whorl and fused towards the base into an elongated tube; petal lobes not imbricate. Petal lobe length: About 4.5 cm. Petal lobe width: About 3.6 cm. Petal lobe shape: Obovate, asymmetrical. Petal lobe apex: Acuminate. Petal lobe margin: Entire; slightly undulate and slightly recurving. Petal lobe texture and luster, upper surface: Smooth, glabrous; velvety. Petal lobe texture and luster, lower surface: Smooth, glabrous; matte. Throat texture: Smooth, glabrous. Tube texture: Smooth, glabrous. Color: Petal lobe, when opening, upper surface: Close to 53A. Petal lobe, when opening, lower surface: Close to 46A. Petal lobe, fully opened, upper surface: Close to 46A; venation, close to 53A; color does not change with development. Petal lobe, fully opened, lower surface: Close to 46A; proximal stripes, close to N155B. Throat: Distally, close to N25C and 45A; proximally, close to N25C; venation, close to N25A. Tube: Distally, close to 53C with stripes, close to 4D; mid-section, close to 4D; proximally, close to 149D.

*Calyx*.—Quantity and arrangement: Five sepals arranged in a single whorl, fused at the base; calyx, star-shaped. Sepal length: About 6.8 mm. Sepal width: About 2.3 mm. Sepal shape: Lanceolate. Sepal apex: Acuminate. Sepal margin: Entire. Sepal texture, upper and lower surfaces: Smooth, glabrous. Sepal color, upper surface: Distally, close to 145C; proximally, close to 145B. Sepal color, lower surface: Distally, close to 145B overlain with close to 179A to 179B; proximally, close to 145A.

*Peduncles*.—Length: About 5.7 cm. Diameter: About 2.5 mm. Texture: Glabrous; rough. Aspect: Upright to outwardly. Color: Close to 143B.

*Pedicels*.—Length: About 1.9 cm. Diameter: About 2.2 mm. Texture: Smooth, glabrous. Aspect: Upright to outwardly. Color: Close to 145A; with development, slightly overlain with close to 179B.

*Reproductive organs*.—Stamens: Quantity and arrangement: Typically five; filaments fused to corolla; anthers, connivent. Anther shape: Lanceolate. Anther size: About 1.5 mm by 8.5 mm. Anther color: Close to 18B. Pollen amount: Scarce. Pollen color: Close to NN155A. Pistils: Quantity: Typically one. Pistil length: About 2.2 cm. Style color: Close to 145C. Stigma shape: Globose. Stigma color: Close to 145B. Ovary color: Close to 144C.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunpa 1463' as illustrated and described.

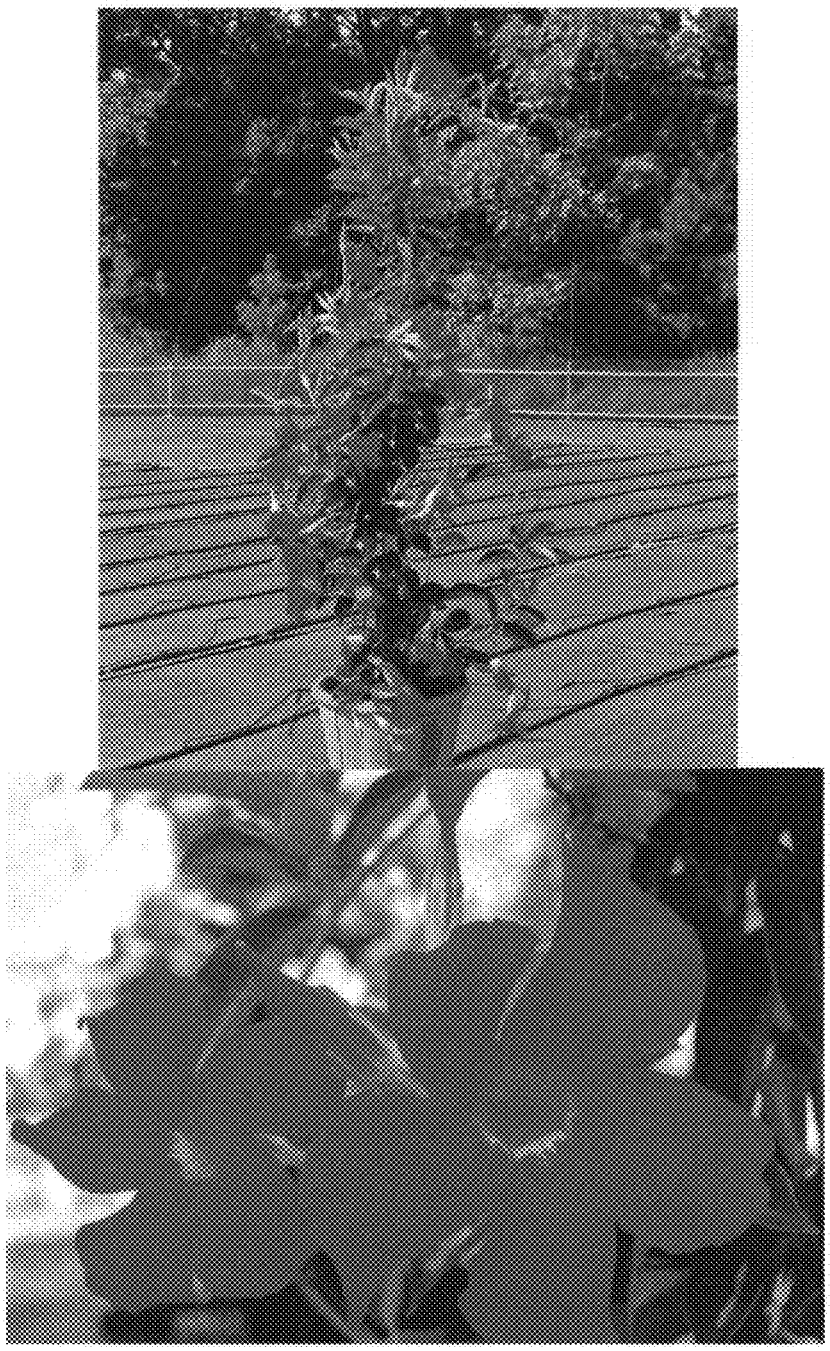

* * * * *